| (12) | United States Patent | (10) Patent No.: | US 9,060,735 B2 |
|---|---|---|---|
| | Yang et al. | (45) Date of Patent: | Jun. 23, 2015 |

(54) CLASSIFICATION OF SEGMENTS OF ACOUSTIC PHYSIOLOGICAL SIGNAL CAPTURED DURING SLEEP USING PHASE-LOCKED LOOP ARRAY

(71) Applicants: Te-Chung Isaac Yang, Aliso Viejo, CA (US); Yungkai Kyle Lai, Irvine, CA (US)

(72) Inventors: Te-Chung Isaac Yang, Aliso Viejo, CA (US); Yungkai Kyle Lai, Irvine, CA (US)

(73) Assignee: Sharp Laboratories of America, Inc., Camas, WA (US)

( * ) Notice: Subject to any disclaimer, the term of this patent is extended or adjusted under 35 U.S.C. 154(b) by 148 days.

(21) Appl. No.: 13/715,137

(22) Filed: Dec. 14, 2012

(65) Prior Publication Data

US 2014/0171815 A1    Jun. 19, 2014

(51) Int. Cl.
  *A61B 7/00*   (2006.01)
  *A61B 5/08*   (2006.01)
  *A61B 5/00*   (2006.01)

(52) U.S. Cl.
  CPC .............. *A61B 5/4818* (2013.01); *A61B 5/7235* (2013.01); *A61B 5/7285* (2013.01); *A61B 5/4812* (2013.01); *A61B 2562/0204* (2013.01)

(58) Field of Classification Search
  USPC .................................................. 600/586, 529
  See application file for complete search history.

(56) References Cited

U.S. PATENT DOCUMENTS

| 4,197,856 | A  | 4/1980 | Northrup |
| 6,278,864 | B1 | 8/2001 | Cummins et al. |
| 6,590,886 | B1 | 7/2003 | Easton et al. |
| 6,731,146 | B1 | 5/2004 | Gallardo |
| 7,039,438 | B2 | 5/2006 | Khlat |

*Primary Examiner* — Brian Szmal
(74) *Attorney, Agent, or Firm* — Scot A. Reader

(57) ABSTRACT

A sleep monitoring method and device classify segments of an acoustic physiological signal captured during sleep as snore and apnea segments. The method and device employ a phase-locked loop array to rapidly detect snore segments for widely variant snoring rhythms exhibited by different people or the same person over time. The phase-locked loop array integrates seamlessly with an apnea timer-thresholding mechanism that detects apnea segments.

10 Claims, 4 Drawing Sheets

CLASSIFICATION OF SEGMENTS OF ACOUSTIC PHYSIOLOGICAL SIGNAL CAPTURED DURING SLEEP USING PHASE-LOCKED LOOP ARRAY

BACKGROUND OF THE INVENTION

The present invention relates to acoustic physiological monitoring and, more particularly, acoustic physiological monitoring during sleep.

Sleep monitoring systems often monitor snoring and apnea. Snoring and apnea are important indicia of sleep quality. Snoring is caused by the obstruction of respiratory airflow through the mouth and nose. Apnea is the cessation of respiratory airflow through the mouth and nose over a sustained period.

Snoring is characterized by rhythmic and loud breath sound. A snore segment in an acoustic physiological signal containing respiration sound may therefore be identified by detecting rhythm and loudness in the signal. Rhythm may be identified in the signal using various signal processing techniques, such as power spectrum density, autocorrelation or phase-locked loop techniques, whereas loudness in the signal may be gauged using various thresholding techniques.

Apnea is characterized by sustained absence of breath sound (i.e., at least ten seconds) interrupted by very loud breath sound (i.e., a snort or gasp as the person struggles to breathe). An apnea segment in an acoustic physiological signal containing respiration sound may therefore be identified by detecting sustained silence in the signal interrupted by a very loud sound in the signal.

Known sleep monitoring systems often suffer from a lack of adequate integration of snore and apnea detection. For example, some sleep monitoring systems do not use the loss of rhythm in an acoustic physiological signal after a snore segment as an indicator of the potential onset of apnea. Moreover, some sleep monitoring systems are ill-equipped to handle widely variant snoring rhythms exhibited by different people or the same person over time.

SUMMARY OF THE INVENTION

The present invention provides a sleep monitoring method and device that classify segments of an acoustic physiological signal captured during sleep as snore and apnea segments. The method and device employ a phase-locked loop array to rapidly detect snore segments for widely variant snoring rhythms exhibited by different people or the same person over time. The phase-locked loop array integrates seamlessly with a apnea timer-thresholding mechanism that detects apnea segments.

In one aspect of the invention, a sleep monitoring device comprises a sound capture element configured to generate an acoustic physiological signal containing respiration sound; an acoustic signal processing element configured to receive from the sound capture element the physiological signal, select a master phase-locked loop to process the physiological signal from a plurality of phase-locked loops based at least in part on rhythm indicators computed by the plurality of phase-locked loops in response to the physiological signal and classify as a snore segment a first segment of the physiological signal while a master rhythm indicator computed by the master phase-locked loop exceeds a snore rhythm threshold; and a sleep data output element configured to output information based at least in part on the snore segment.

In some embodiments, the master phase-locked loop is selected based on a determination that the master rhythm indicator has a highest confidence value among the rhythm indicators.

In some embodiments, the plurality of phase-locked loops have different free run frequencies.

In some embodiments, the processing element is further configured to apply to the physiological signal a plurality of bandpass filters having different passbands optimized for the plurality of phase-locked loops.

In some embodiments, the processing element is further configured to determine that the physiological signal exceeds a snore loudness threshold.

In some embodiments, the processing element is further configured to classify as an apnea segment a second segment of the physiological signal in response to determining that the physiological signal exceeds a gasp threshold more than a predetermined time after the master rhythm indicator falls below the snore rhythm threshold, and the output element is further configured to output information based at least in part on the apnea segment.

In some embodiments, the processing element is further configured to apply a respiration sound bandpass pre-filter to the physiological signal.

In some embodiments, the processing element is further configured to compute an energy envelope of the physiological signal.

In some embodiments, the processing element is further configured to normalize the physiological signal.

In another aspect of the invention, a sleep monitoring device comprises a sound capture element configured to generate an acoustic physiological signal containing respiration sound; an acoustic signal processing element configured to receive from the sound capture element the physiological signal, classify as a snore segment a first segment of the physiological signal while a rhythm indicator computed by a phase-locked loop in response to the physiological signal exceeds a snore rhythm threshold and classify as an apnea segment a second segment of the physiological signal in response to determining that the physiological signal exceeds a gasp threshold more than a predetermined time after the rhythm indicator falls below the snore rhythm threshold; and a sleep data output element configured to output information based at least in part on the snore segment and the apnea segment.

In some embodiments, the processing element is further configured to determine that the physiological signal exceeds a snore loudness threshold.

In some embodiments, the gasp threshold is higher than the snore loudness threshold.

In some embodiments, the predetermined time is ten seconds.

In some embodiments, the processing element is further configured to select a master phase-locked loop to process the physiological signal from a plurality of phase-locked loops based at least in part on rhythm indicators computed by the plurality of phase-locked loops in response to the physiological signal.

In yet another aspect of the invention, a sleep monitoring method comprises the steps of generating by a sleep monitoring device an acoustic physiological signal containing respiration sound; selecting by the device a master phase-locked loop to process the physiological signal from a plurality of phase-locked loops based at least in part on rhythm indicators computed by the plurality of phase-locked loops in response to the physiological signal; classifying by the device as a snore segment a first segment of the physiological signal while a master rhythm indicator computed by the master phase-locked loop exceeds a snore rhythm threshold; and outputting by the device information based at least in part on the snore segment.

In some embodiments, the method further comprises the steps of classifying by the device as an apnea segment a second segment of the physiological signal in response to determining that the physiological signal exceeds a gasp threshold more than a predetermined time after the master rhythm indicator falls below the snore rhythm threshold; and outputting by the device information based at least in part on the apnea segment.

In some embodiments, the master phase-locked loop is selected based on a determination that the master rhythm indicator has a highest confidence value among the rhythm indicators.

In some embodiments, the plurality of phase-locked loops have different free run frequencies.

In some embodiments, the method further comprises the step of applying to the physiological signal a plurality of bandpass filters having different passbands optimized for the plurality of phase-locked loops.

In some embodiments, the method further comprises the step of determining that the physiological signal exceeds a snore loudness threshold.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
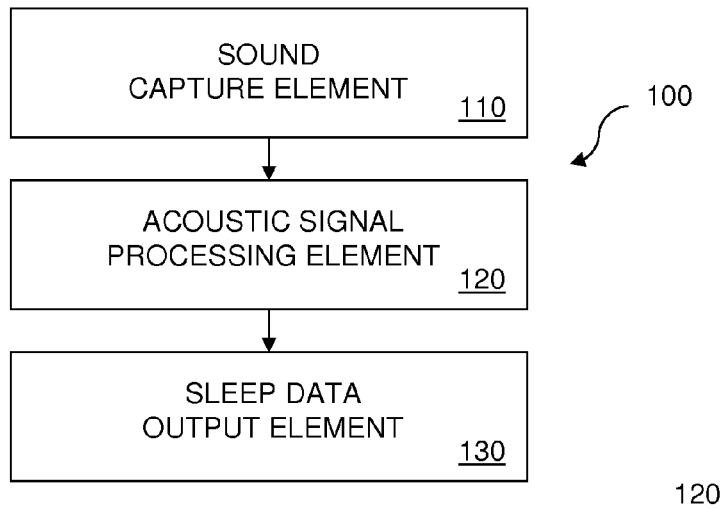
FIG. 1 shows a sleep monitoring device in some embodiments of the invention.

FIG. 1 shows a sleep monitoring device 100 in some embodiments of the invention. Monitoring device 100 includes a sound capture element 110, an acoustic signal processing element 120 and a sleep data output element 130, which are communicatively coupled in series.

Capture element 110 includes a sound transducer, such as a microphone, that continually detects body sound, such as respiration sound, heart sound and other sound, while a person is sleeping. The sound transducer is positioned at a detection point, such as the chest, of a person being monitored during sleep, and continually transmits a acoustic physiological signal containing the detected body sound to processing element 120. Capture element 110 may also include an amplifier, a lowpass filter and an analog/digital (A/D) converter that transform the detected body sound into the physiological signal. Body sound is represented in the physiological signal as a time sequence of digital samples having varying amplitudes.

Processing element 120, under control of a processor executing software instructions, receives the physiological signal from capture system 110, classifies different time segments of the physiological signal as snore segments, apnea segments and other segments and transmits the segment classifications to output element 130. Processing element 120 may additionally generate and transmit to output element 130 values for physiological parameters, such as respiration rate.

Figure 2:
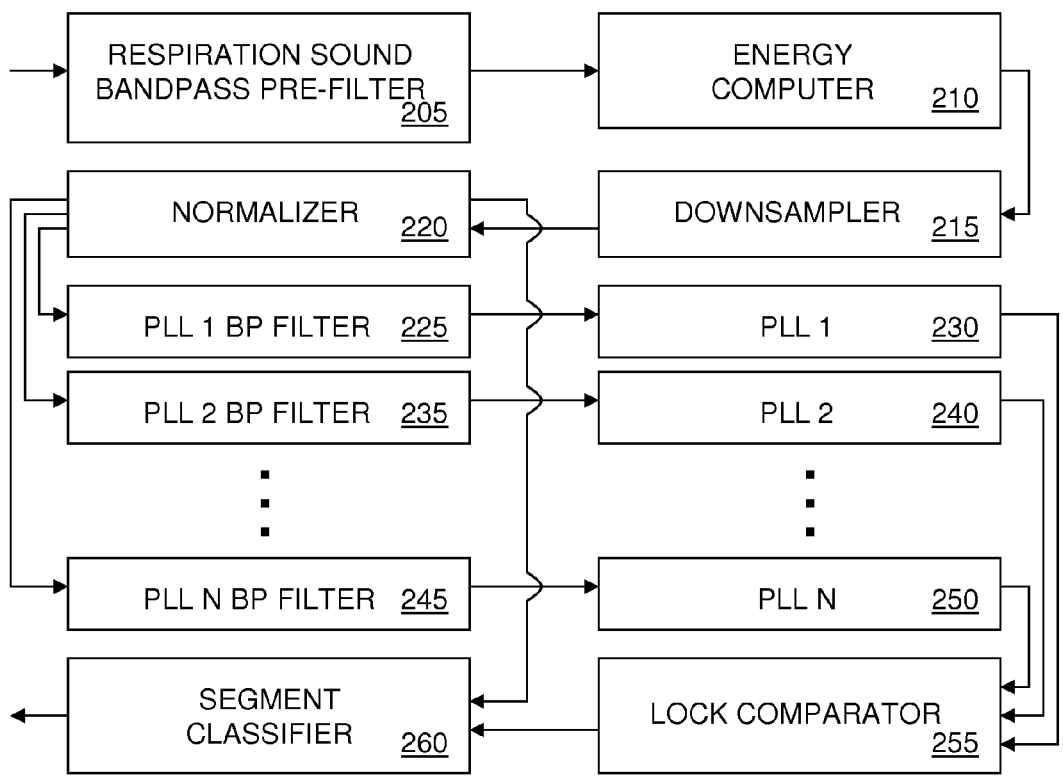
FIG. 2 shows an acoustic signal processing element in some embodiments of the invention.

FIG. 2 shows processing element 120 in some embodiments of the invention. Processing element 120 classifies different time segments of the physiological signal as snore segments, apnea segments and other segments by performing a sleep monitoring method wherein processing element 120 transitions between a snore detection stage, a snoring stage and an apnea detection stage.

Figure 3:
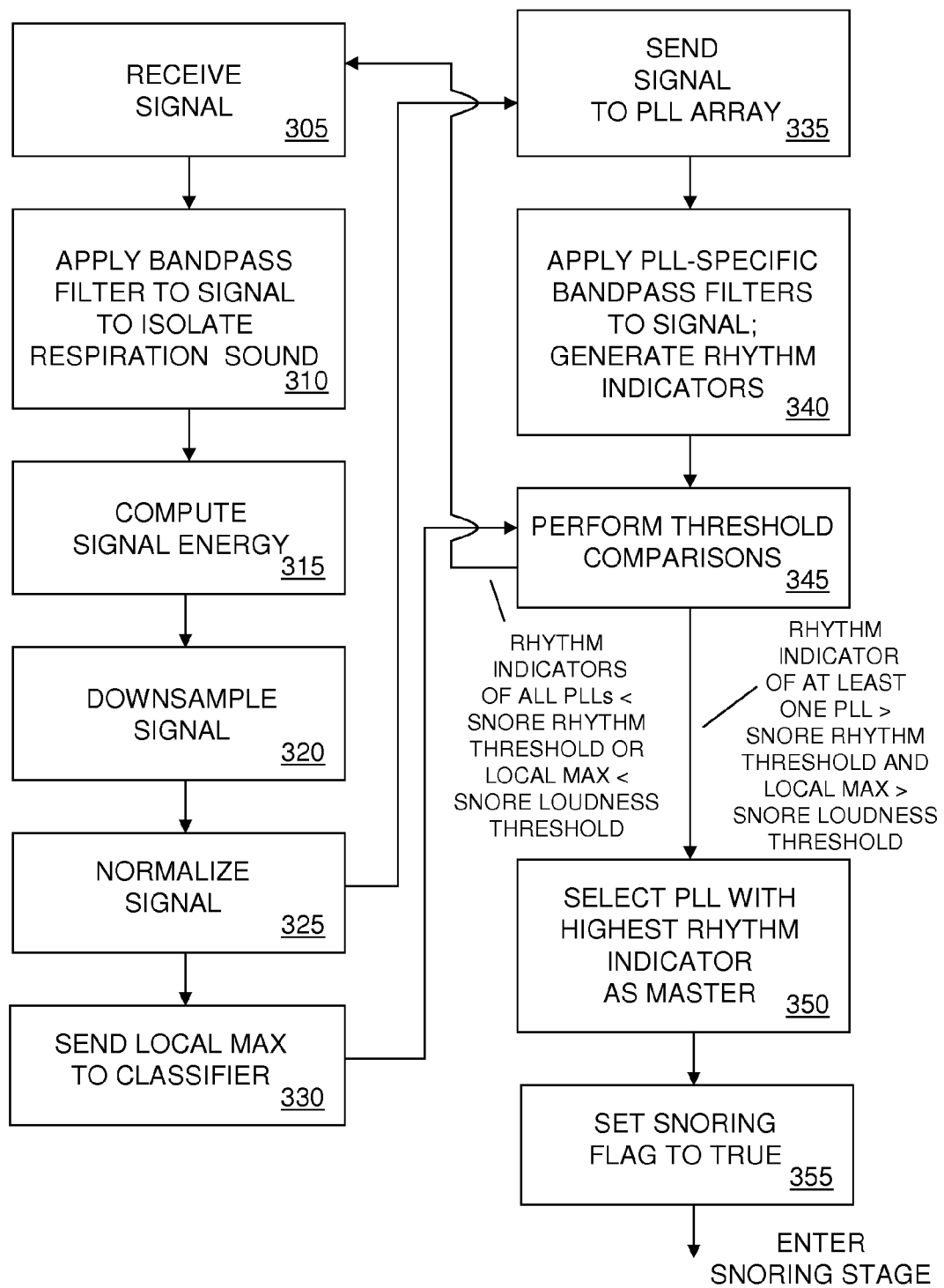
FIG. 3 shows a snore detection stage of a sleep monitoring method in some embodiments of the invention.

FIG. 3 shows a snore detection stage of a sleep monitoring method in some embodiments of the invention. When monitoring device 100 is initialized, processing element 120 begins receiving the physiological signal from capture element 110 (305). Respiration sound, heart sound and other sound are intermingled in the physiological signal as received by processing element 120. Processing element 120 applies a respiration sound bandpass pre-filter 205 to the physiological signal to provide rough isolation of breathing and snoring sound and remove other sound (310). Pre-filter 205 has a passband in the frequency domain of breathing and snoring sound. In some embodiments, pre-filter 205 has a passband from 100 Hz to 600 Hz.

After application of pre-filter 205, an energy computer 210 computes an energy envelope representing the total energy of the physiological signal during short time windows (315). In some embodiments, the length of each time window is between five percent and ten percent of a complete respiration cycle. It bears noting that the loudness of sound is generally in proportion to the amplitude of data points in the energy envelope. Thus, troughs in the energy envelope generally represent times between breathing and snoring whereas peaks and spikes in an energy signal generally represent breathing and snoring.

After energy computer 210, downsampler 215 downsamples the physiological signal to a lower sampling rate (320). As the number of human respiration cycles typically varies between about three and twenty per minute (i.e., 1/20 Hz to 1/3 Hz), a downsampling factor of 100 (i.e., from 3200 Hz to 32 Hz) is applied in some embodiments to preserve the respiration sound of interest while reducing memory requirements and computational complexity of monitoring device 100.

After downsampler 215, normalizer 220 range-bounds the physiological signal between −1 and +1 (325). As the energy envelope of the physiological signal is always positive, and as phase locked-loops 230, 240, . . . 250 expect a signal that oscillates over time between positive and negative, normalizer 220 first applies a highpass filter that removes the DC energy component of the physiological signal. Normalizer 220 next normalizes the physiological signal by dividing the energy of the current window by a global maximum (GM) computed using the energy of previous windows. In this normalization process, normalizer 220 first identifies a maximum energy from the absolute value of a number of immediately preceding windows, excepting the current window. The maximum energy is deemed the local maximum (LM). By way of example, the number of immediately preceding windows used to determine the local maximum may include all windows from the previous twenty seconds. Next, normalizer 220 determines whether the local maximum is greater than or less than the global maximum. Next, normalizer 220 updates the global maximum according to the formula $$GM_N = LM*p + GM_{N-1}*(1-p)$$

where p is selected to be between 0.5 and one if the local maximum is greater than the global maximum and p is selected to be between zero and 0.5 if the global maximum is greater than the local maximum. In some embodiments, p is assigned a value of 0.6 where the local maximum is greater than the global maximum and 0.3 where the global maximum is greater than the local maximum. Normalizer 220 then updates the energy of the current window by dividing the energy of the current window by the global maximum. In some embodiments, normalizer 220 proceeds to apply a clipping function to the energy of the current window to ensure that the value remains between −1 and +1.

Normalizer 220 provides the local maximum to a segment classifier 260 (330) and provides the physiological signal to a phase-locked loop array for parallel processing (335). In this regard, if the physiological signal is sufficiently rhythmic, as exhibited by high confidence in phase lock, it may reflect the beginning of a snore segment. On the other hand, if the physiological signal is insufficiently rhythmic, as exhibited by low confidence in phase lock, it does not reflect the beginning of a snore segment. Moreover, as snoring rhythms exhibited by different people or the same person over time are widely variant, the phase-locked loop array includes a multiple of phase-locked loops (PLL 1, 2, ... N) 230, 240, ... 250 having different free run frequencies and proceeded by a respective multiple of phase-locked loop bandpass filters (PLL 1, 2, ... 3 BP FILTERS) 225, 235, ... 245 having different passbands optimized for the different phase-locked loops 230, 240, ... 250, which ensures rapid acquisition of the snoring rhythm regardless who is being monitored and the time of monitoring. Bandpass filters 225, 235, ... 245 and corresponding phase-locked loops 230, 240, ... 250 operate on the physiological signal in parallel, putting respective local oscillator waveforms associated with loops 230, 240, ... 250 in locked phase with the physiological signal and producing respective rhythm indicators indicative of confidence in the phase lock (340).

For example, phase-locked loop 230 may be designed to lock a very slow snoring rhythm of three cycles per minute and may have a free run frequency (Ff) of 1/20 Hz and a lock range from 3/80 Hz to 1/15 Hz (i.e., from 3/4*Ff to 4/3*Ff). Phase-locked loop bandpass filter 225 preceding phase-locked loop 230 may have a low cutoff frequency of 1/30 Hz (i.e., 2/3*Ff) and a high cutoff frequency of 3/40 Hz (i.e., 3/2*Ff). In that event, one of parallel instances of the physiological signal is applied to filter 225 followed by loop 230 where the physiological signal is filtered and the phase of a local oscillator waveform associated with loop 230 is locked to the phase of the physiological signal. More particularly, filter 225 filters the physiological signal to remove sound outside of the lock range of loop 230. After filtering, the physiological signal resembles a sinusoidal waveform bounded between −1 and +1. Loop 230 then estimates a phase difference between the physiological signal and a local oscillator waveform associated with loop 230 as the product (P) of the physiological signal and the local oscillator waveform. The local oscillator waveform is a pure sinusoidal waveform that initially operates at the free run frequency of loop 230 (i.e., 1/20 Hz). Loop 230 then estimates a driving force (DF) required to put the local oscillator waveform in locked phase with the physiological signal. The driving force estimate is computed according to the formula $$DF_N = DF_{N-1} + Ki*P_N + Kp*P_N - Kp*P_{N-1}$$

where Ki and Kp are constants that represent characteristics of a low pass filter applied to the product. In some embodiments, Ki and Kp are determined by the formulas $$Ki = (0.5*\pi/f)^2; Kp = [\pi/f/\text{sqrt}(2)] - Ki$$

where f is the sampling frequency of the physiological signal after downsampling.

For the initial driving force estimate, $DF_{N-1}$ and $P_{N-1}$ may be assigned predetermined values. Loop 230 next updates the phase (PH) of the local oscillator waveform according to the formula $$PH_N = PH_{N-1} + DF_N$$

Loop 230 repeats the process on subsequent time domain components of the physiological signal and computes a rhythm indicator as a time-averaged product of the local oscillator waveform and the physiological signal at a ninety degree phase shift over a short time window. The rhythm indicator is measure of confidence in the phase lock achieved by loop 230.

Meanwhile, similar filtering and phase-locking operations are performed by filters 235 ... 245 and loops 240 ... 250 on other instances of the physiological signal in parallel using different filter passbands and different free run frequencies to lock phase and generate other rhythm indicators.

Next, processing element 120 performs threshold comparisons (345). Lock comparator 255 determines from the rhythm indicators computed independently by phase-locked loops 230, 240, ... 250 whether the physiological signal is sufficiently rhythmic to potentially reflect the beginning of a snore segment. In this regard, snoring is characterized by rhythmic and loud breath sound. Lock comparator 255 determines whether any rhythm indicator exceeds a snore rhythm threshold. If at least one rhythm indicator exceeds the snore rhythm threshold, the physiological signal is sufficiently rhythmic to reflect the beginning of a snore segment. On the other hand, if no rhythm indicator exceeds the snore rhythm threshold, the physiological signal is insufficiently rhythmic to reflect the beginning of a snore segment. If multiple rhythm indicators exceed the snore rhythm threshold, lock comparator 255 further determines which one of phase-locked loops 230, 240, ... 250 whose rhythm indicator is exceeds the snore rhythm threshold is the highest (i.e., highest confidence in phase lock). Lock comparator 255 provides the results of these determinations to segment classifier 260.

Segment classifier 260 definitively determines from the local maximum provided by normalizer 220 and the information provided by lock comparator 255 whether the physiological signal reflects the beginning of a snore segment. More particularly, segment classifier 260 compares the local maximum with a snore loudness threshold. If the local maximum exceeds the snore loudness threshold, the physiological signal is sufficiently loud that it may reflect the beginning of a snore segment. On the other hand, if the local maximum does not exceed the snore loudness threshold, the physiological signal is insufficiently loud to reflect the beginning of a snore segment. Segment classifier 260 further determines from the results provided by lock comparator 255 whether the physiological signal is sufficiently rhythmic to reflect the beginning of a snore segment. If the physiological signal is both sufficiently loud and rhythmic to be the beginning of a snore segment, segment classifier 260 determines that the physiological signal reflects the beginning of a snore segment and processing system 120 transitions to the snoring stage. More particularly, segment classifier 260 designates the one of phase-locked loops 230, 240, ... 250 whose rhythm indicator is the highest (i.e., highest confidence in phase lock) as the master phase-locked loop (350) and sets the snoring flag to true (355) causing entry into the snoring stage. On the other hand, if the local maximum does not exceed the snore loudness threshold or the results provided by lock comparator 255 indicate that the physiological signal is insufficiently rhythmic to reflect the beginning of a snore segment, processing element 120 remains in the snore detection stage where the physiological signal provided by capture element 110 is continually processed until transition to snoring stage is indicated.

Figure 4:
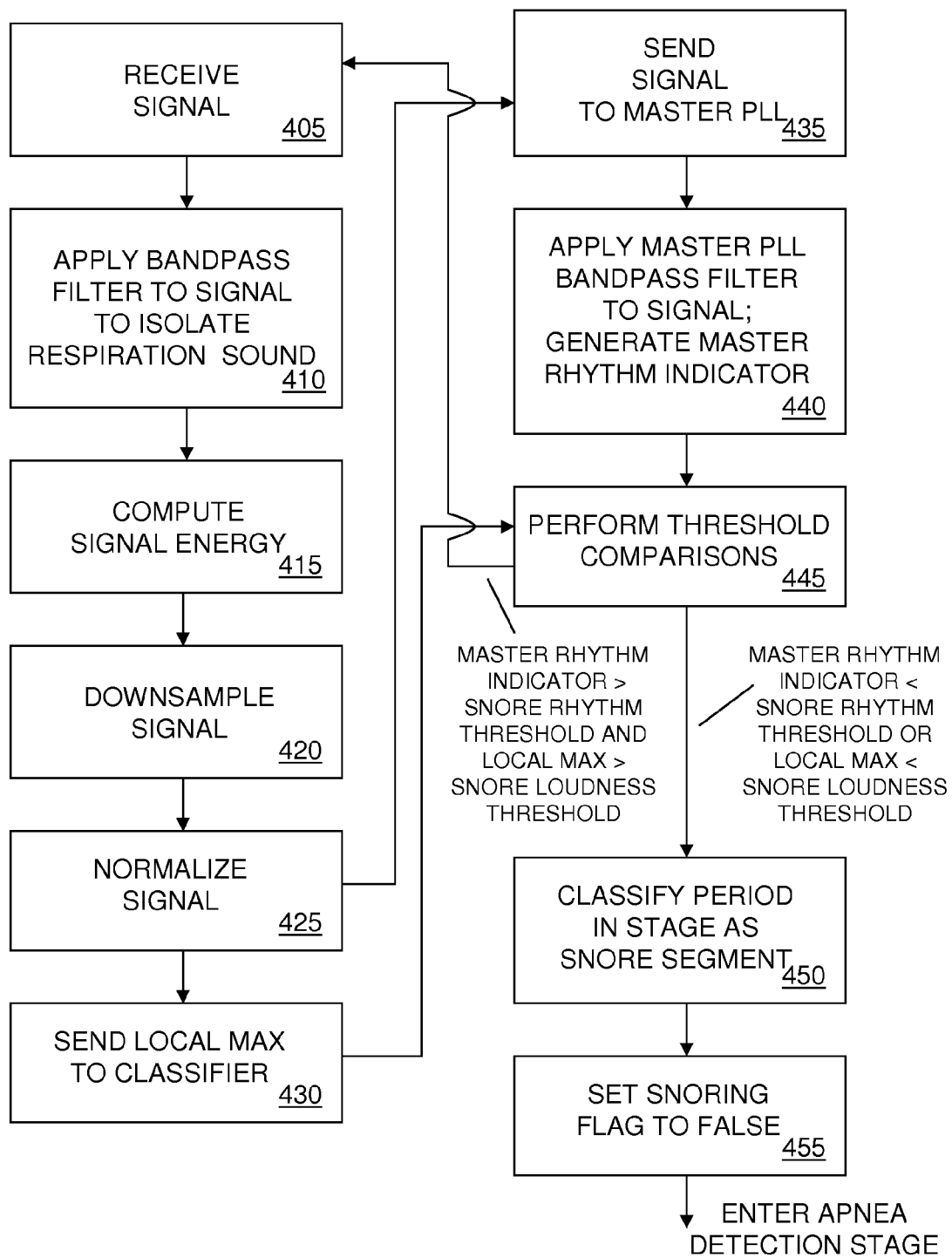
FIG. 4 shows a snoring stage of a sleep monitoring method in some embodiments of the invention.

FIG. 4 shows a snoring stage of a sleep monitoring method in some embodiments of the invention. In the snoring stage, processing element 120 continues to receive the physiological signal from capture element 110 (405), apply bandpass pre-filter 205 to the physiological signal (410), compute the energy of physiological signal (415), downsample the physiological signal (420) normalize the physiological signal (425) and provide the local maximum to segment classifier 260 (430). However, the physiological signal is processed only by the one of phase-locked loops 230, 240, ... 250 that has been designated the master by segment classifier 260 (and the corresponding one of bandpass filters 225, 235, . . . 245) (435). The master phase-locked loop and corresponding bandpass filter are applied to the physiological signal to keep the local oscillator waveform associated with the master phase-locked loop in locked phase with the physiological signal and produce a master rhythm indicator indicative of confidence in the phase lock (440). In threshold comparisons performed by processing element 120 (445), segment classifier 260 determines from the local maximum provided by normalizer 220 and results provided by lock comparator 255 whether the physiological signal reflects a continuation of a snore segment or the potential start of an apnea segment. In this regard, since apnea is characterized by a period of sustained silence (i.e., at least ten seconds) after a period of snoring, the loss of loudness or rhythm in the physiological signal characteristic of snoring may represent the onset of apnea. Segment classifier 260 compares the local maximum with the snore loudness threshold. As long as the local maximum exceeds the snore loudness threshold, the energy of the present physiological signal remains sufficiently high that it may be part of a snore segment. On the other hand, when the present local maximum falls below the snore loudness threshold, the energy of the present physiological signal is no longer sufficiently high to be part of a snore segment and may reflect the start of an apnea segment. Segment classifier 260 further determines from results provided by lock comparator 255 whether the master rhythm indicator continues to exceed the snore rhythm threshold. As long as the master rhythm indicator continues to exceed the snore rhythm threshold, the physiological signal remains sufficiently rhythmic to be part of a snore segment. On the other hand, when the master rhythm indicator falls below the snore rhythm threshold, the physiological signal is no longer sufficiently rhythmic to be part of a snore segment and may reflect the start of an apnea segment. Therefore, as long as both the local maximum exceeds the snore loudness threshold and the master rhythm indicator exceeds the snore rhythm threshold, processing element 120 remains in the snoring stage where the physiological signal provided by capture element 110 is continually processed until transition to apnea detection stage is indicated. On the other hand, when the local maximum falls below the snore loudness threshold or the master rhythm indicator falls below the snore rhythm threshold, segment classifier 260 classifies the period spent in the snoring stage as a snore segment (450) and sets the snoring flag to false (455), prompting processing system 120 to enter into the apnea detection stage.

Figure 5:
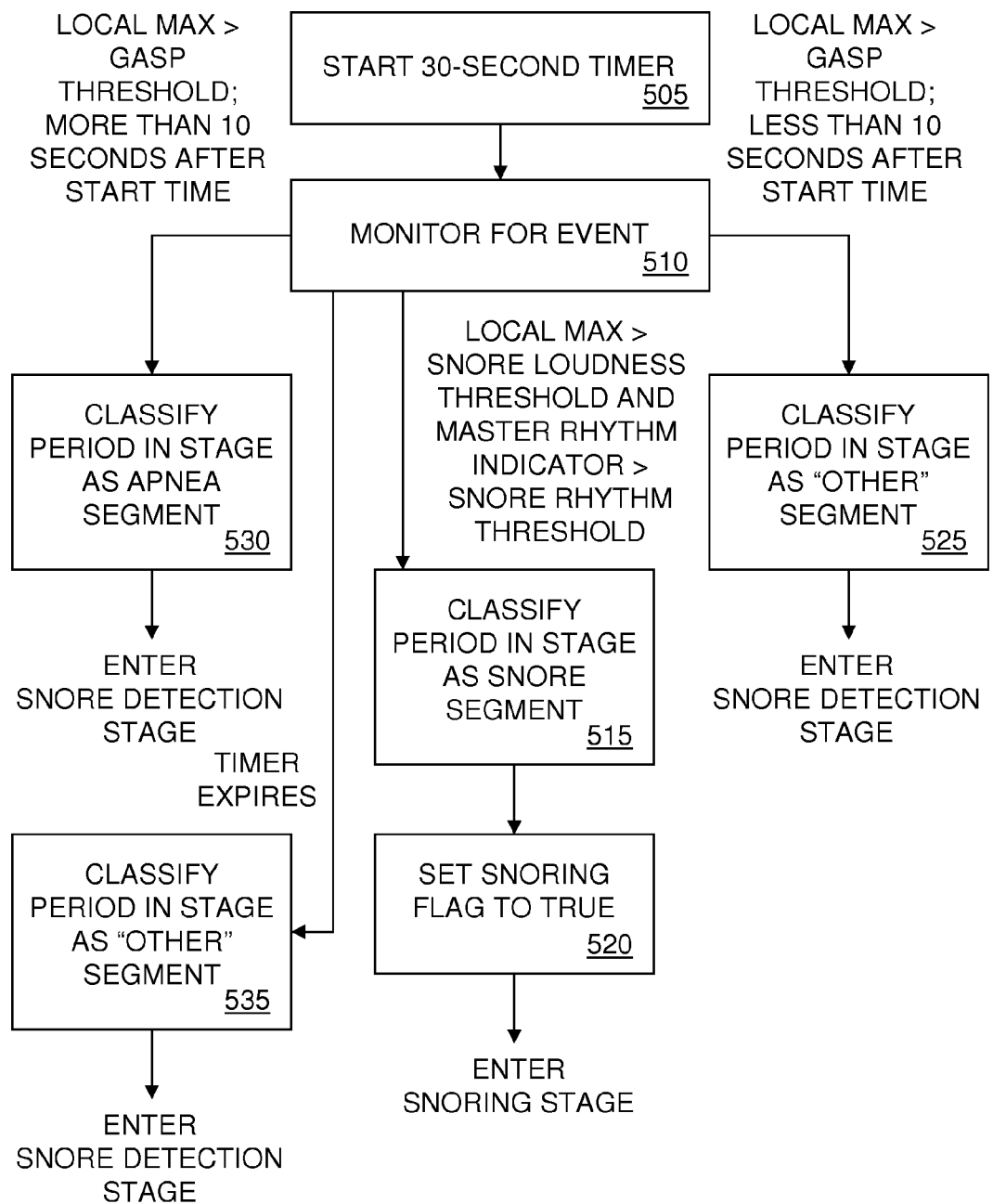
FIG. 5 shows an apnea detection stage of a sleep monitoring method in some embodiments of the invention.

FIG. 5 shows an apnea detection stage of a sleep monitoring method in some embodiments of the invention. In the apnea detection stage, processing element 120 continues to monitor loudness and rhythm of the physiological signal as in the snoring stage but also temporarily monitors for apnea. Segment classifier 260 starts a 30-second timer (505) and monitors for one of several events (510). A first type of event is a return of loudness and rhythm to the physiological signal indicative of snoring, as evidenced by the local maximum exceeding the snore loudness threshold and the master rhythm indicator exceeding the snore rhythm threshold. In that event, segment classifier 260 classifies the period spent in the apnea detection stage as a continuation of the previous snore segment (520) and sets the snoring flag to true (525), whereupon processing element 120 reenters the snoring stage. A second type of event is a noise indicative of other than apnea, as evidenced by the local maximum exceeding a gasp threshold, which is a loudness threshold set higher than the snore loudness threshold, less than ten seconds after the start of the timer. In that event, segment classifier 260 classifies the period spent in the apnea detection stage as an "other" segment (i.e., other than apnea) (525) and processing element 120 reenters the snore detection stage. A third type of event is a gasp indicative of apnea, as evidenced by the local maximum exceeding the gasp threshold more than ten seconds and less than thirty seconds after the start of the timer. In that event, segment classifier 260 classifies the period spent in the apnea detection stage as an apnea segment (530) and processing element 120 reenters the snore detection stage. A fourth type of event is a timer expiration event thirty seconds after start of the timer. In that event, segment classifier 260 classifies the period spent in the apnea detection stage as an "other" segment (i.e., other than apnea) (535) and processing element 120 reenters the snore detection stage.

Processing element 120 transmits sleep profile data to output element 130. Sleep profile data may include segment classifications and/or sleep parameter data determined using segment classifications. Output element 130 has a display screen for displaying sleep profile data received from processing element 120 and/or information derived from sleep profile data, such as numerical scores or color-coded indicators. In some embodiments, output element 130, in addition to a display screen, has an interface to an internal or external data management system that stores sleep profile data and/or an interface that transmits such data to a remote monitoring device, such as a monitoring device at a clinician facility.

In some embodiments, processing element 120 performs at least some of the processing operations described herein in custom circuitry.

In some embodiments, capture system 110, processing element 120 and output element 130 are coupled via wired communication links. In other embodiments, two or more of capture element 110, processing element 120 and output element 130 are coupled via one or more wireless communication links.

It will be appreciated by those of ordinary skill in the art that the invention can be embodied in other specific forms without departing from the spirit or essential character hereof. The present description is considered in all respects to be illustrative and not restrictive. The scope of the invention is indicated by the appended claims, and all changes that come with in the meaning and range of equivalents thereof are intended to be embraced therein.

What is claimed is:

1. A sleep monitoring method, comprising the steps of:
 detecting by a sleep monitoring device, using a sound transducer, respiration sound;
 generating by the device, using the sound transducer, an acoustic physiological signal representing the respiration sound;
 selecting by the device a master phase-locked loop to process the physiological signal from a plurality of phase-locked loops based at least in part on rhythm indicators computed by the plurality of phase-locked loops in response to the physiological signal;
 classifying by the device as a snore segment a first segment of the physiological signal while a master rhythm indicator computed by the master phase-locked loop exceeds a snore rhythm threshold;
 generating by the device sleep profile data based at least in part on the snore segment; and
 outputting by the device information based at least in part on the sleep profile data.

2. The monitoring method of claim 1, further comprising the step of classifying by the device as an apnea segment a second segment of the physiological signal in response to determining that the physiological signal exceeds a gasp threshold more than a predetermined time after the master rhythm indicator falls below the snore rhythm threshold,
 wherein the sleep profile data are generated based further on the apnea segment.

3. The monitoring method of claim 2, further comprising the step of determining that the physiological signal exceeds a snore loudness threshold.

4. The monitoring method of claim 3, wherein the gasp threshold is higher than the snore loudness threshold.

5. The monitoring method of claim 1, wherein the master phase-locked loop is selected based on a determination that the master rhythm indicator has a highest confidence value among the rhythm indicators.

6. The monitoring method of claim 1, wherein the plurality of phase-locked loops have different free run frequencies.

7. The monitoring method of claim 1, further comprising the step of applying to the physiological signal a plurality of bandpass filters having different passbands optimized for the plurality of phase-locked loops.

8. The monitoring method of claim 1, further comprising the step of computing an energy envelope of the physiological signal.

9. The monitoring method of claim 1, further comprising the step of normalizing the physiological signal.

10. A sleep monitoring method, comprising the steps of:
 detecting by a sleep monitoring device respiration sound;
 generating by the device an acoustic physiological signal representing the respiration sound;
 selecting by the device a master phase-locked loop to process the physiological signal from a plurality of phase-locked loops using rhythm indicators computed by the plurality of phase-locked loops in response to the physiological signal;
 classifying by the device as a snore segment a first segment of the physiological signal while a master rhythm indicator computed by the master phase-locked loop exceeds a snore rhythm threshold;
 classifying by the device as an apnea segment a second segment of the physiological signal after the snore segment in response to determining that the physiological signal exceeds a gasp threshold more than a predetermined time after the master rhythm indicator falls below the snore rhythm threshold;
 generating by the device sleep profile data using the snore segment and the apnea segment; and
 outputting by the device information using the sleep profile data.

* * * * *